US012661461B2

(12) United States Patent
Toddywala et al.

(10) Patent No.: US 12,661,461 B2
(45) Date of Patent: Jun. 23, 2026

(54) BREATH ACTUATED NEBULIZER

(71) Applicant: Flexicare (Group) Limited, Mid Glamorgan (GB)

(72) Inventors: Rohinton D. Toddywala, Somerset, NJ (US); Vijay Shukla, Somerset, NJ (US); K. Mosaddeq Hossain, Somerset, NJ (US)

(73) Assignee: Flexicare (Group) Limited, Mid Glamorgan (GB)

( * ) Notice: Subject to any disclaimer, the term of this patent is extended or adjusted under 35 U.S.C. 154(b) by 542 days.

(21) Appl. No.: 18/025,534

(22) PCT Filed: Sep. 9, 2021

(86) PCT No.: PCT/US2021/071404
§ 371 (c)(1),
(2) Date: Mar. 9, 2023

(87) PCT Pub. No.: WO2022/056535
PCT Pub. Date: Mar. 17, 2022

(65) Prior Publication Data
US 2023/0330358 A1      Oct. 19, 2023

Related U.S. Application Data

(60) Provisional application No. 63/076,446, filed on Sep. 10, 2020.

(51) Int. Cl.
*A61M 11/06* (2006.01)
*A61M 15/00* (2006.01)
(Continued)

(52) U.S. Cl.
CPC ........ *A61M 11/06* (2013.01); *A61M 15/0015* (2014.02); *A61M 15/0021* (2014.02);
(Continued)

(58) Field of Classification Search
CPC .............. A61M 11/06; A61M 15/0015; A61M 15/0021; A61M 16/06; A61M 16/0833;
(Continued)

(56) References Cited

U.S. PATENT DOCUMENTS 4,588,129 A    5/1986  Shanks
5,823,179 A    10/1998  Grychowski et al.
(Continued)

FOREIGN PATENT DOCUMENTS

CN       207356334 U  *  5/2018
EP        281650 A  *  3/1987  ............ A61M 15/00
(Continued)

OTHER PUBLICATIONS

Translation EP281650 accessed Sep. 30, 2025 (Year: 2025).*
(Continued)

*Primary Examiner* — Elliot S Ruddie
(74) *Attorney, Agent, or Firm* — Robert D. Buyan; Stout, Uxa & Buyan, LLP

(57) ABSTRACT

A breath-actuated jet nebulizer is provided, having a body enclosing a gas jet that creates a Venturi effect. The Venturi requires a baffle in close proximity to the gas jet. The baffle is movable in response to the inhalation of the patient, such that the baffle has a default (resting) position distal to the gas jet such that no Venturi effect is created, and no nebulization occurs. During the inhalation phase of a breathing cycle, a diaphragm flexes and pushes the baffle into close proximity with the Venturi gas jet, such that a Venturi effect is created that causes a low pressure zone in proximity to one or more liquid orifices that draw a drug solution into the Venturi, where the solution is nebulized. Also disclosed is an exhalation filter to prevent infectious particles from the patient from escaping and endangering nearby caregivers.

16 Claims, 8 Drawing Sheets

(51) Int. Cl.
  *A61M 16/06*  (2006.01)
  *A61M 16/08*  (2006.01)
  *A61M 16/10*  (2006.01)

(52) U.S. Cl.
  CPC ........ *A61M 16/06* (2013.01); *A61M 16/0833* (2014.02); *A61M 16/1065* (2014.02); *A61M 2205/581* (2013.01)

(58) Field of Classification Search
  CPC ........ A61M 16/1065; A61M 2205/581; A61M 16/0093; A61M 2205/59; A61M 11/002; A61M 15/0018; A61M 15/0091–0096
  See application file for complete search history.

(56)                References Cited

U.S. PATENT DOCUMENTS

| | | | |
|---|---|---|---|
| 6,644,304 | B2 | 11/2003 | Grychowski et al. |
| RE40,591 | E | 12/2008 | Denyer |

| | | | | |
|---|---|---|---|---|
| 2013/0327323 | A1* | 12/2013 | Rubin | A61M 16/1065 |
| | | | | 128/200.14 |
| 2016/0228656 | A1* | 8/2016 | Vasandani | A61M 16/1065 |

FOREIGN PATENT DOCUMENTS

| | | | |
|---|---|---|---|
| EP | 0281650 | A1 | 9/1988 |
| WO | WO2012173992 | A1 | 12/2012 |
| WO | WO2015009920 | A1 | 1/2015 |

OTHER PUBLICATIONS

Translation CN207356334U accessed Sep. 30, 2025 (Year: 2025).*
PCT International Search Report dated Feb. 9, 2022 in related PCT Application No. PCT/US2021/071404.
J. Samuel and G. Smaldone, "Maximizing Deep Lung Deposition in Healthy and Fibrotic Subjects During Jet Nebulization," J. Aerosol Med. Pulmonary Drug Delivery, vol. 33, No. 2, 2020, pp. 108-115.

* cited by examiner

° Aerosol
« Compressed Gas
↟ Air from the Atmosphere

° Compressed Gas

BREATH ACTUATED NEBULIZER

CROSS REFERENCE TO RELATED APPLICATION

This patent application is a national stage filing under 35 U.S.C. $371 of Patent Cooperation Treaty International Application No. PCT/US2021/071404, filed Sep. 9, 2021 entitled Breath Actuated Nebulizer, which claims priority to U.S. Provisional Patent Application No. 63/076,446 filed Sep. 10, 2020, the entire disclosure of each such application being expressly incorporated herein by reference.

FIELD OF THE INVENTION

This disclosure pertains to nebulizers for the administration of inhaled aerosol drugs.

BACKGROUND

In the field of respiratory devices, nebulizers are important devices used for the inhalation of drugs in the form of an aerosol to patients in need of a drug administered directly into the lungs. A nebulizer employs an apparatus that generates an aerosol or mist from a solution (usually an aqueous solution) or suspension of a drug. The mist may be an aerosolized suspension or an atomized suspension of drug, meaning micro-droplets suspended in air, medical oxygen, or other inhalable gas. The aerosol is conveyed to the mouth and/or nose of a patient and inhaled into the lungs. In some cases, the mist is conveyed to the lungs through a mouthpiece. In other cases, the nebulizer may be coupled to an inhalation mask.

Several nebulization technologies are known, including gas-jet, ultrasonic, and vibrating mesh nebulizers.

This disclosure pertains to gas-jet nebulizers, which operate using a Venturi, wherein a jet of pressurized gas (air or other suitable gas, such as medical oxygen) is directed over an orifice on a capillary that is connected to a reservoir containing a drug in aqueous solution. The Venturi creates a localized low-pressure zone that draws the drug solution out of the capillary orifice and into the air jet, where the liquid is atomized by a shearing effect. Typically, a baffle is employed in the jet effluent to assist in the formation of appropriate size droplets in the nebulized stream. In addition, a baffle prevents large droplets from exiting the device, so that only aerosol micro-droplets of drug containing solution exit the device. Still further, in many nebulizer designs, a baffle may be required to deflect the low pressure zone created by a Venturi jet over a liquid orifice in communication with the drug reservoir In such designs, the baffle is required to draw the liquid into the stream of pressurized gas that causes nebulization of the liquid. An example of such a nebulizer is disclosed in U.S. Pat. No. 4,588,129. The aerosol is then inhaled by the patient. Typically, the aerosol production is continuous, so a vent is typically provided to ensure that the pressure differential created by the jet operates continuously and consistently. The drug reservoir in nebulizers is usually a cone, cup, or bowl-shaped vessel into which a sterile aqueous solution of the drug is added.

Typical drugs used with nebulizers are drugs for the treatment of asthma and obstructive pulmonary diseases, but other pulmonary and systematic medications may be administered by inhalation with nebulizers. For example, albuterol (called salbutamol in many countries), used for treating asthma and bronchospasm, may be administered as a nebulized solution. Other examples of drugs administered by nebulization include formoterol and ipratropium. Another example is pentamidine, a drug used to treat *Pneumocystis carinii* pneumonia (PCP) (also called *Pneumocystis firovech*). Many other medications are useful or potentially useful as inhaled drugs and can potentially be used with a nebulizer.

Nebulizers are particularly useful for the administration of inhaled drugs to small children, elderly, unconscious, or disabled patients who cannot coordinate their breathing or take instruction on the use of coordinated inhalation devices, such as a metered dose inhaler. Also, nebulizers may be used with an inhalation mask for patients who cannot use a mouthpiece to inhale the drug. With a nebulizer, the dose of drug is administered to the patient over a period of several minutes, and possibly ten to twenty (or more) tidal or slow deep inhalations per minute, so breathing coordination is not required.

Nebulizers are typically equipped with a mouthpiece that a patient can insert in their mouth, making an airtight seal with their lips while inhaling through the mouth to ingest the nebulized medication into the lungs. In the case of patients who cannot hold a mouthpiece in their mouth or close their lips round the mouthpiece to create a seal, an inhalation mask may be used with a nebulizer. An example of such a mask is disclosed in PCT International Application WO 2012/173993.

In breath-actuated nebulizers, nebulization of the drug only occurs during inhalation by the patient. Breath-actuated nebulizers have a means for stopping the nebulization or flow of aerosol during exhalation or other intervals when the patient is neither inhaling nor exhaling. Such devices are known, for example, from Denyer in United States Patent RE40591, and Grychowski et al., in U.S. Pat. Nos. 5,823, 179 and 6,644,304. A breath-actuated nebulizer has been marketed in the United States under the brand name AEROECLIPSE® by Monaghan Medical, and by Trudell Medical International in other countries.

Breath-actuated nebulizers may have significant advantages over conventional nebulizers. In conventional nebulizers, the drug is aerosolized continuously regardless of whether the patient is inhaling or not. Conventional nebulizers typically are vented to the atmosphere, so aerosol that is not inhaled is vented to the air in front of the patient. This wastes drug and exposes others (including caregivers) in the vicinity to the aerosolized drug. In addition, the dosage is impossible to be determined precisely because of this drug loss. In many cases, these shortcomings are not a problem, due to the low cost of conventional (continuous) nebulizers, and the low toxicity and low cost of drug of many of the drugs used in conventional nebulizers.

However, in the case of expensive drugs or drugs that may be toxic or sensitizing to others in the vicinity of the patient, conventional nebulizers are much less desirable than a breath-actuated nebulizer. With a breath-actuated nebulizer, the dosage can be precisely measured, and very little of the drug is wasted, since nebulization is stopped when the patient is not inhaling. A horizontally oriented breath triggered gas-jet nebulizer was disclosed in U.S. Pat. No. 10,463,813-B2 to Vasandani et al.

SUMMARY OF THE INVENTION

In an embodiment, this invention provides a breath triggered gas jet nebulizer comprising a generally cylindrical body in a vertical orientation to the patient (parallel to the patient's face). Within the body is a Venturi configured to nebulize a solution of a drug stored in a reservoir. Within the body is a shaft integrated with a baffle and diaphragm that moves horizontally in response to the breathing of a patient. When the patient is inhaling the diaphragm flexes shifting the baffle toward the patient and over the Venturi, allowing nebulization to occur. When the patient's inhalation stops, the diaphragm flexes to a default position in which the baffle is shifted to a position distal to the Venturi, thereby stopping the nebulization.

In an embodiment, a breath actuated nebulizer is provided for the administration of inhaled medication to a patient only during the inhalation portion of a breathing cycle. The nebulizer may include a vertically oriented cylindrical upper body defining an input upper chamber airway nested inside an output upper chamber airway, and having a one-way inhalation valve at the top of the input upper chamber and a vertically oriented lower body having a chamber therein defining a liquid reservoir containing a medicament in solution, wherein said liquid reservoir defines the horizontal axis. A pressurized gas inlet port may be provided, that is in fluid communication with a gas jet at the interface of the upper body and the lower body wherein the gas jet is aimed vertically upward in the center of the input upper airway. In an embodiment, a vertically oriented liquid channel is surrounding or adjacent to the gas inlet port, wherein the bottom of the liquid channel is in fluid communication with the liquid reservoir and the top of the liquid channel is a liquid orifice adjacent to the gas jet.

In an embodiment, a horizontally movable baffle is provided having a first baffle position at a predetermined distance from the gas jet such that a pressure differential from a Venturi effect is created in the liquid channel that draws the medicament solution through the liquid channel and causes nebulization of the medicament solution by the interaction of the gas jet and liquid orifice. The baffle may have a second default baffle position distal from the gas jet so that the pressure differential in the liquid channel is insufficient to draw liquid into the liquid channel, and no nebulization of the liquid occurs when the patient is not breathing. In an embodiment, the baffle moves in a horizontal channel between the first and second positions at a fixed vertical distance relative to the gas jet, and the baffle movement from the second position to the first position is controlled in response to the motion of a diaphragm that moves in response to the inhalation by the patient. The diaphragm is in mechanical communication with the baffle such that the diaphragm movement during inhalation moves the baffle to the first position, and the diaphragm shifts to a default position when the patient is not inhaling and baffle shifts to the second position. The nebulized medicament solution generated by this apparatus is inhaled by the patient via an output airway on a horizontal orientation in fluid communication with the gas jet, thereby delivering the nebulized medicament solution to the lungs of the patient.

DETAILED DESCRIPTION

Figure 1:
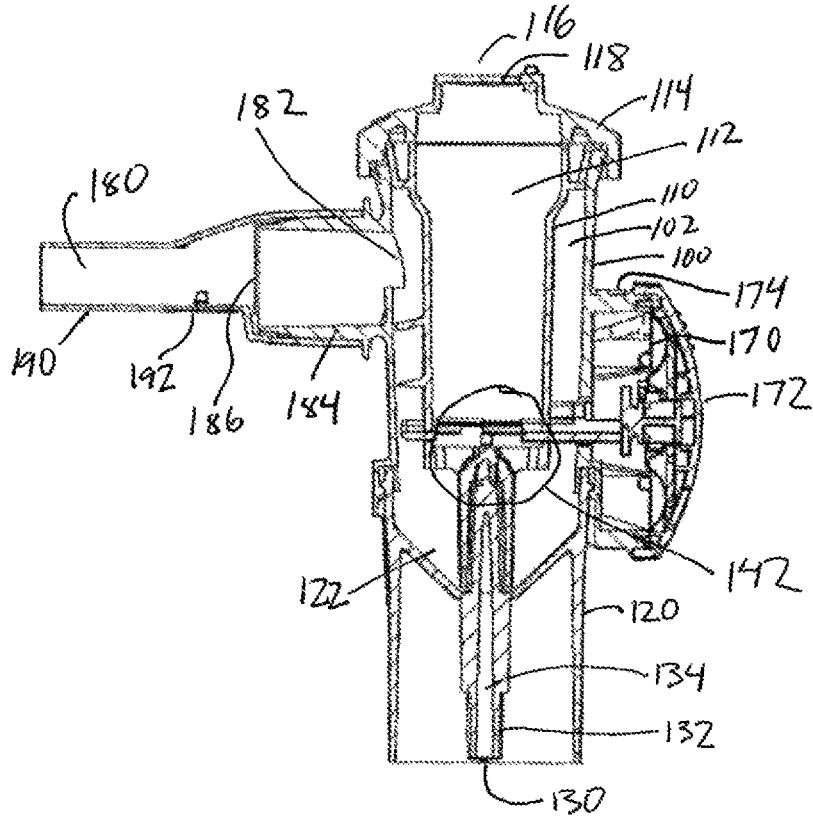
FIG. 1 is a cross-section view of the nebulizer according to an embodiment of the present invention. The circle marked "A" is the section shown in further detail in FIGS. 4-6.

Reference is made herein to orientation terms such as top, bottom, vertical, and horizontal. Because the inventive nebulizer has a liquid reservoir 122, the device must be used in a generally upright orientation as shown in the figures. This upright orientation is termed herein "vertical oriented," or a "vertically orientation." These orientation terms have the meanings as illustrated in the figures. Thus, with reference to FIG. 1, item 116 is at the top of the inventive device, 130 is at the bottom. The vertical orientation runs from the top to the bottom (i.e., in a line (not shown) from the center of 116 to 130). The horizontal orientation, also termed herein a "horizontal axis," runs from right to left as shown in FIG. 1, in a perpendicular orientation with respect to the vertical orientation. Terms such as upper and lower are in relation to these definitions of top and bottom.

The nebulization action in the gas jet nebulizers disclosed herein for administering medication to humans or animals by inhalation depends on a device with a reservoir containing a solution with a drug dissolved therein, and a Venturi effect with a high pressure jet orifice and one or more liquid orifices adjacent to the jet, wherein a baffle or deflector impinges on the jet a short distance above the jet orifice. One or more liquid orifices adjacent to the Venturi orifice are in communication with liquid tubes or capillaries fed by a drug reservoir containing a solution of drug. The nebulization or aerosolization (these terms are used interchangeably herein), presumably occurs because the baffle deflects the low-pressure zone created by the Venturi over the liquid orifices. Without being bound by any theory of operation, it is believed that the reduced pressure created by the Venturi jet impinging on the baffle draws the drug solution through the liquid orifices, and the jet aerosolizes the liquid as it exits the liquid orifices from shearing effects. The baffle typically also performs a secondary function of deflecting large droplets and forcing them back into the drug reservoir, since in a drug nebulizer, only very small droplets that freely float in air are desired as an inhaled aerosol.

Without the baffle, the liquid orifices are presumably not subject to the effect of the Venturi low pressure zone and no liquid is drawn out of the liquid orifices, and no aerosolization occurs. Thus, in this invention, a movable baffle is provided in a horizontal plane, such that when the baffle is directly over the Venturi, nebulization occurs, and when the baffle is moved horizontally away from the Venturi, nebulization stops. In this invention, by moving the baffle into a nebulizing position in response to the inhalation of a patient, the nebulization only occurs during the inhalation portion of a breathing cycle, when the patient is inhaling, and no nebulization occurs when the patient is exhaling or otherwise not exerting an inhalation. This movement of the baffle that creates or stops nebulization is termed "breath triggered" or "breath actuated" (which terms are used interchangeably) nebulization. In an embodiment, the inventive nebulizer may have a mode, controlled by a selector knob, in which nebulization is constant. In this embodiment, the selector knob may have a different position in which breath actuated nebulization occurs.

To briefly summarize the operation of the inventive device, ambient air is ingested through opening 116 into an input airway 112, and a nebulized aerosol of a drug solution is introduced into the air flow at Venturi section 142. The air flow with aerosol then proceeds downward slightly to clear the bottom rim of upper internal body 110 and rises to the level of exit port 182 through an output airway. The downward dip and rise of the airflow tend to ensure that only aerosol droplets of appropriate size are inhaled by the patient. The air flow with aerosol is then inhaled by the patient via airway 180 and mouthpiece 190. During exhalation, exhaled air is vented though one-way exhalation valve 182 to the exterior of the nebulizer. The nebulization is controlled by a movable baffle 160 that has a default (or resting) position distal from the gas jet that drives the Venturi, and a nebulization position in which baffle 160 moves, under the influence of an inspiratory action, to cover the Venturi jet, which creates a Venturi effect that draws a liquid drug solution through liquid channel 150 where the liquid is nebulized from shear effects in the gas jet. The gas jet is driven by an air flow at about 50 psi. A diaphragm that flexes in response to an inhalation by the patient drives the movement of baffle 160.

Figure 4A:
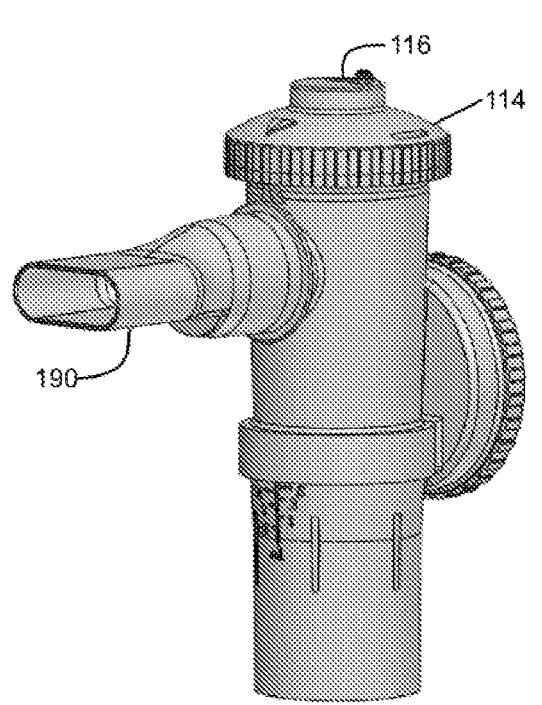
FIG. 4A is an isometric view of an embodiment of the inventive nebulizer looking towards a mouthpiece.
Figure 4B:
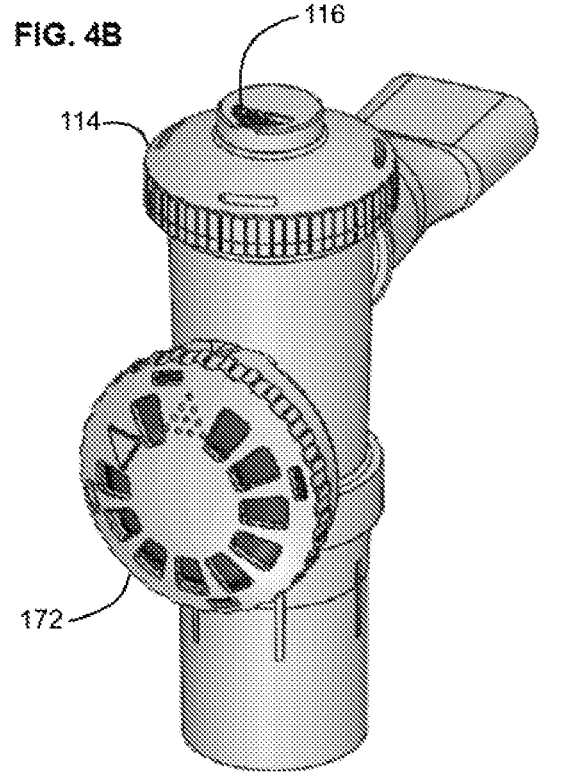
FIG. 4B is an isometric view of an embodiment of the inventive nebulizer showing a selector knob in the position for breath-actuated nebulization.
Figure 4C:
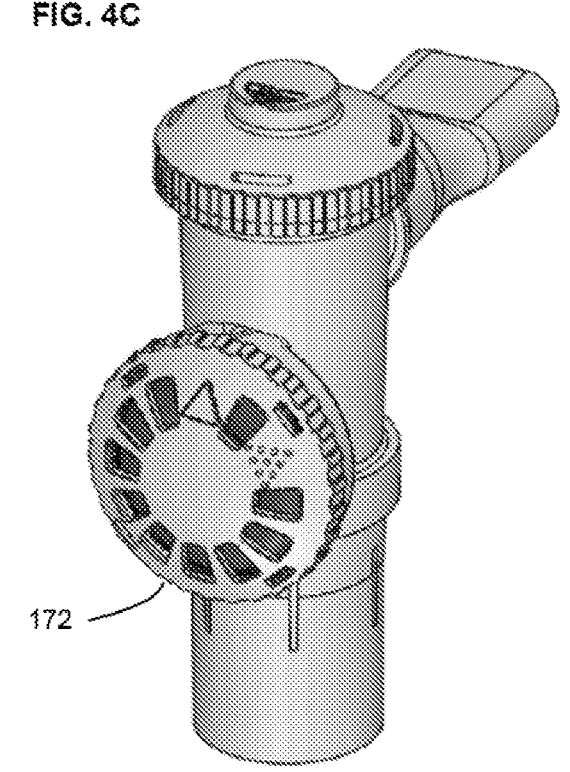
FIG. 4C is an isometric view of an embodiment of the inventive nebulizer showing a selector knob in the position so that nebulization is continuous.
Figure 5A:
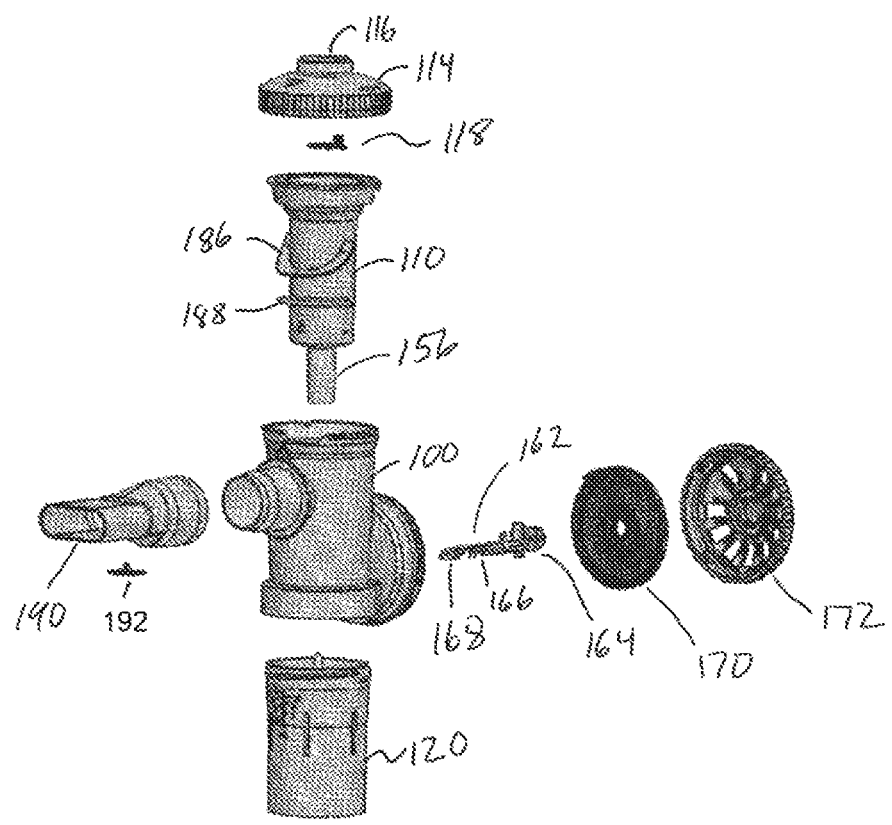
FIG. 5A is an exploded view showing interior parts of the embodiment of FIGS. 1-4.
Figure 5B:
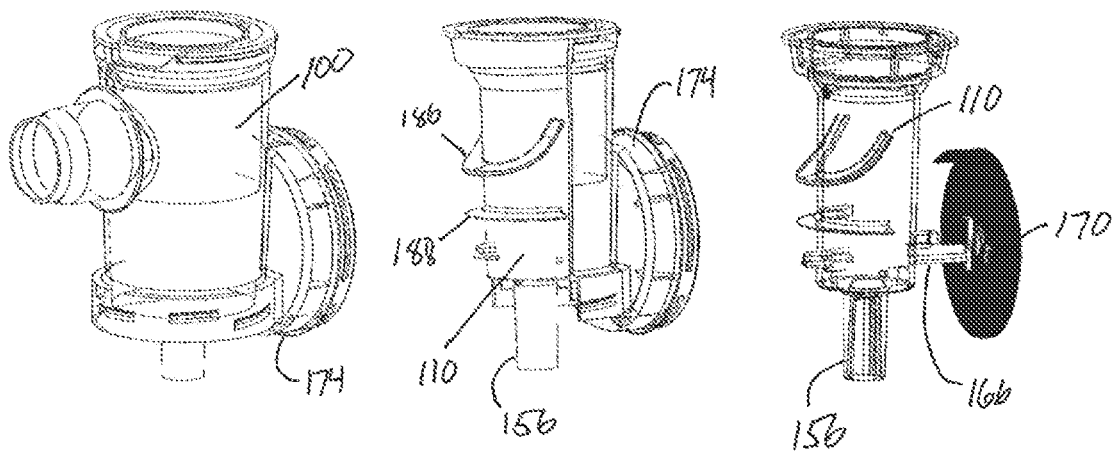
FIG. 5B has various cutaway views of internal part of the inventive nebulizer.

In an embodiment illustrated in the figures, this invention provides a breath actuated nebulizer for the administration of inhaled medication to a patient only during the inhalation portion of a breathing cycle, having a cylindrical and vertically oriented upper body 100 defining an output upper chamber airway 102, with a vertically oriented internal body 110 nested within upper body 100, wherein the internal body 110 defines an input upper chamber airway 112, and having a one-way inhalation valve 118 at the top 116 of the input upper chamber airway 112. The top 116 of airway 112 is an inhalation input port. Also provided is a vertically oriented lower body 120 having a chamber 122 therein defining a liquid reservoir containing a medicament in solution 124, wherein said liquid reservoir defines the horizontal axis. A cross-section view is shown in FIG. 1, and several exterior views are shown in FIGS. 4A-4C.

As used herein, a medicament solution is a solution containing a drug that can be administered to patients by inhalation. Typically, such drugs are dissolved in water or a physiologically compatible buffer solution. The solution is converted to an aerosol by any of several possible nebulization methods. The aerosol of the drug is then inhaled to deliver the drug to the lungs of the patient. Typically, an aerosol droplet size of 1 μm to 5 μm is considered ideal. Control of the droplet size is discussed elsewhere herein.

In an embodiment, a pressurized air inlet port 130 defined by pressurized air inlet tube 132 is in fluid communication via pressurized air channel 134 with a gas jet 140 at the interface of the upper body and the lower body wherein the gas jet 140 is aimed vertically upward in the center of the input upper airway. The parts around gas jet 140 are also termed herein the Venturi section 142. In an embodiment, also provided is a vertically oriented liquid channel 150 surrounding or adjacent to the pressurized air inlet tube 132, wherein the bottom of liquid channel 150 defines liquid input port 152. Liquid channel 150 is in fluid communication with the liquid reservoir 122 and the top of the liquid channel, comprising is a liquid orifice 154 adjacent to the gas jet 140. In the embodiment as illustrated, liquid channel 150 is defined by the interior of stem 156 and the exterior of pressurized air inlet tube 132. In this embodiment, liquid channel 150 has an annular cross section.

Gas jet 140 requires a pressurized air supply to drive the Venturi effect. Typically, this is 50 psi (3.5 bar). The pressurized air is supplied through pressurized air channel 134.

Figure 6:
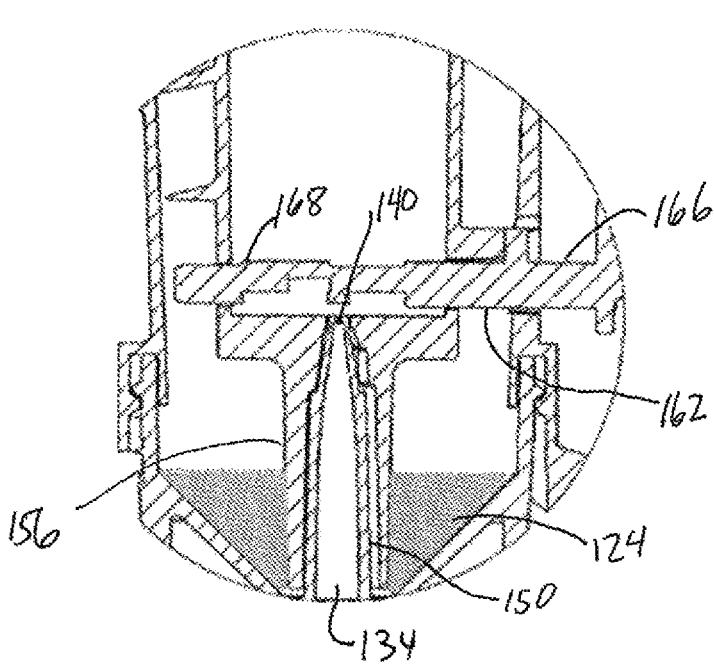
FIG. 6 is a cross section view of the configuration of the Venturi section (142 in FIG. 1) with the gas jet and baffle during continuous nebulization.
Figure 7A:
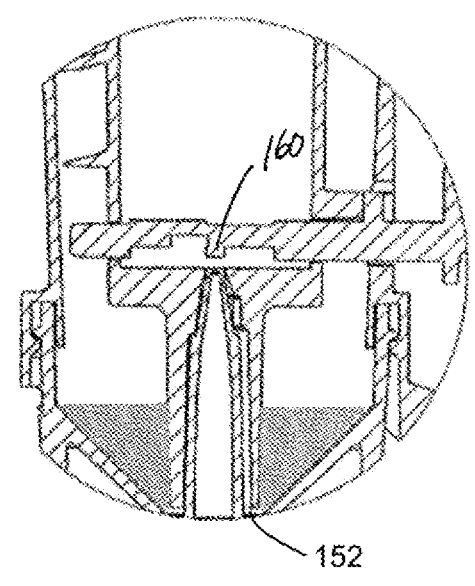
FIG. 7A is a cross section view of the configuration of the gas jet and baffle (142 in FIG. 1) during inhalation in the breath actuated nebulization mode.
Figure 8:
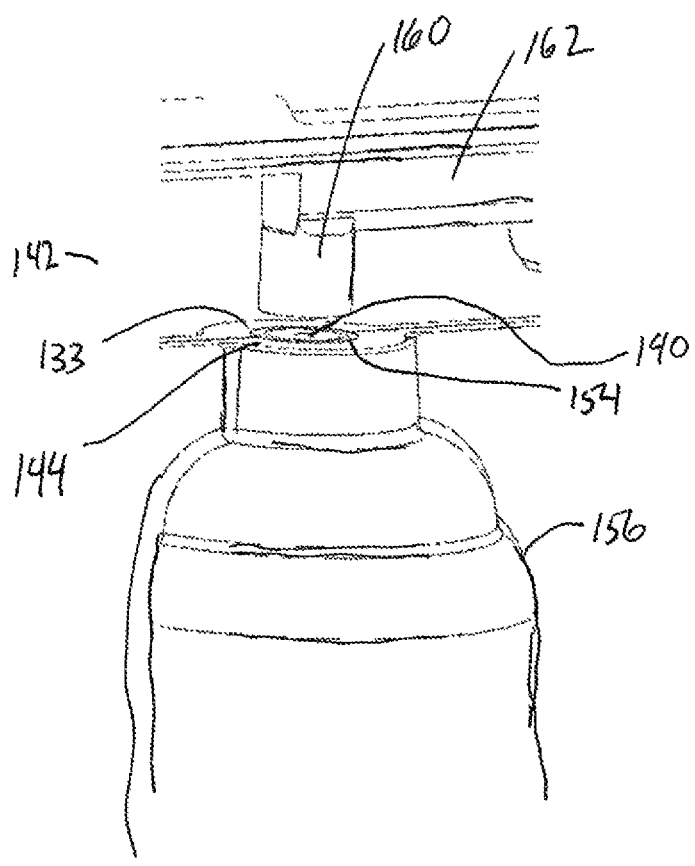
FIG. 8 is a detail view of the Venturi section in an embodiment of the inventive jet nebulizer.

An interior view of the Venturi section 142 is shown in FIG. 8. Stem 156, which may be integral with the internal body 110 (not shown) tapers towards surface 144 which is the top of stem 156. Nested within surface 144 is surface 133, which is the top of pressurized air inlet tube 132. The gap between 144 and 133 defines annular liquid orifice 154. Gas jet 140 is in the center of air inlet tube 132. Also shown in FIG. 8 is baffle 160 shown in the position illustrated in FIGS. 6 and 7A, and baffle member 162. As shown in FIG. 8, the liquid orifice comprises a concentric tubular opening in a concentric relationship to the gas jet. Alternatively, the liquid orifice may comprise one or more holes on top of the liquid channel. As shown in FIG. 8, the gas jet and liquid orifice are on the same horizontal plane.

The breath actuation is controlled by a horizontally movable baffle 160 having a first baffle position (shown in FIG. 7A) at a predetermined distance from the gas jet 140 such that a pressure differential is created in the liquid channel 150 that draws the medicament solution through the liquid channel and causes nebulization of the medicament solution 124 by the interaction of the gas jet 140 and liquid orifice 154.

In an embodiment, the baffle 160 has a second position (FIG. 7B) distal from the gas jet 140 so that the pressure differential in the liquid channel 150 is insufficient to draw liquid into the liquid channel, and no nebulization of the liquid occurs. This second position is the default baffle position, where the baffle rests when the patient is not inhaling. Thus, the baffle 160 moves in a horizontal channel between the first and second positions at a fixed vertical distance relative to gas jet 140.

Baffle 160 is part of a baffle member 162 that includes several parts, including a mechanical linkage 164 to diaphragm 170, a baffle rail 166, and baffle head 168. In an embodiment, baffle member 162 is a unitary part, formed from a single piece of plastic or other material. Baffle 160 is a relatively small portion of baffle head 168 that has a flat or nearly flat surface of sufficient size to create a Venturi effect when baffle 160 is oriented directly above gas jet 140. When the baffle member is in the second position, other portions (e.g., 161) of baffle head 168 are above the gas jet, and these other portions are not capable of causing the Venturi effect, so no nebulization occurs.

Movement of baffle member 162 in turn is controlled by diaphragm 170. The baffle member 162 is moved from the second position to the first position in response to the motion of diaphragm 170 that moves in response to the inhalation by the patient. In an embodiment, the diaphragm is in mechanical communication with baffle member 162 through mechanical linkage 164. Thus, when the diaphragm flexes inward towards the Venturi section 142, baffle member 162 is forced into the position illustrated in FIG. 7A to cause nebulization to occur. When the patient inhales, a negative pressure is drawn through the upper chamber airway 102 which is in fluid communication with diaphragm 170 that causes diaphragm 170 to flex inward.

Figure 7B:
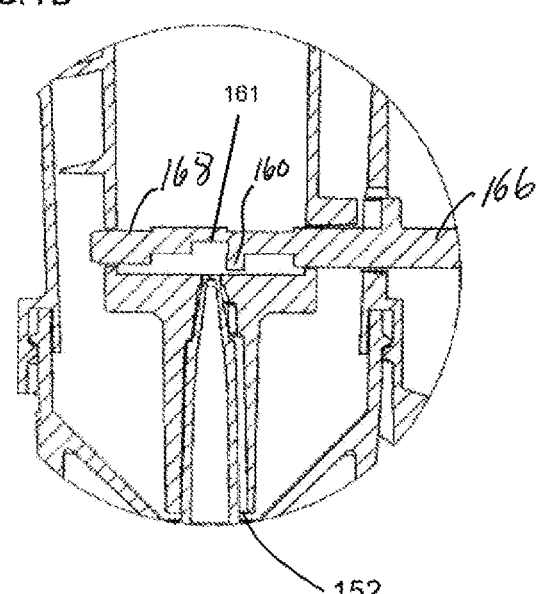
FIG. 7B is a cross section view of the configuration of the gas jet and baffle (142 in FIG. 1) during non-inhalation when nebulization is deactivated.

When the patient is not inhaling, that is, during other parts of the breathing cycle such as exhalation or neither inhaling or exhaling, the diaphragm 170 shifts to a default position distal to the Venturi section 142. This causes the baffle member 162 and baffle 160 to shift to the second position as shown in FIG. 7B, where no nebulization occurs.

The diaphragm 170 must be designed to be sufficiently sensitive to low inhalation flow velocities, for example from highly diseased persons with very weak inspiratory ability, or small children, yet still provide sufficient force to move the shaft to the nebulization position. In an embodiment, the diaphragm may be designed to move within a range of inhalation flow rates of 0.5 L/min in newborn infants to 15 L/min in adults.

In an embodiment, the baffle is configured so that an audio signal is produced when the baffle moves from the first position to the second position. The audio signal may be a clicking sound produced by a trigger contacting a part of the side cover.

After the drug solution 124 is nebulized in the Venturi section, the nebulized medicament solution travels to the mouth of the patient via output upper chamber airway 102 and horizontal airway 180, in fluid communication with the gas jet, thereby delivering the nebulized medicament solution to the lungs of the patient.

Figure 2:
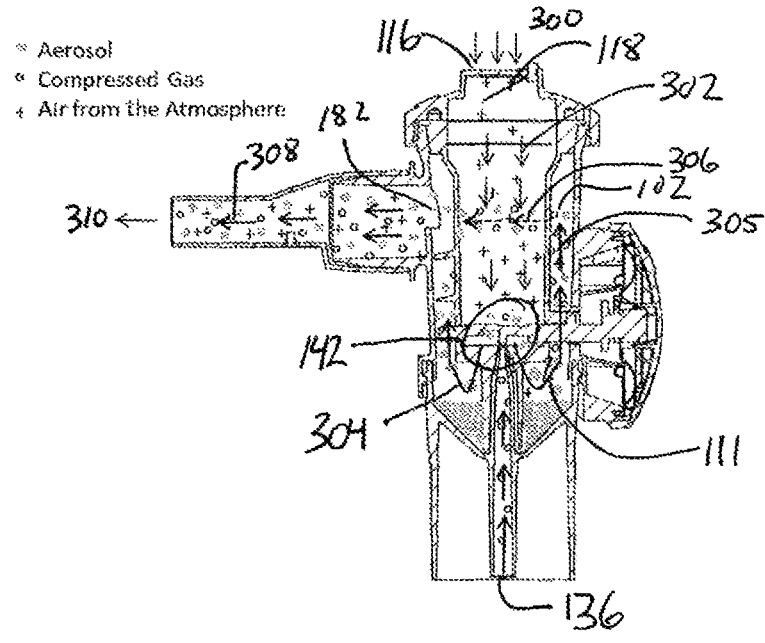
FIG. 2 is a cross-section view of the nebulizer according to an embodiment of the present invention, showing the air flow and aerosol flow schematically during inhalation when nebulization is active.
Figure 3:
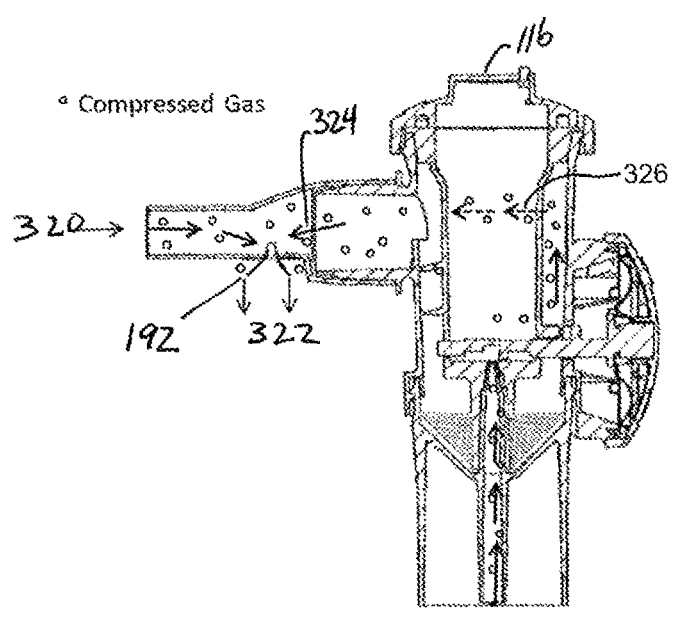
FIG. 3 is a cross-section view of the nebulizer according to an embodiment of the present invention, showing the air flow and aerosol flow schematically during exhalation when nebulization is inactive.

The flow of gases and aerosol in the nebulizer is shown in FIGS. 2 and 3. During an inhalation, a negative pressure is drawn on the interior of the entire apparatus. This causes ambient air 300 to enter input port 116 via one-way inhalation valve 116 (in the open position in FIG. 2) and travel down input upper chamber airway 112 (arrows 302) to Venturi section 142. As described above, during an inhalation, baffle 160 is in the position illustrated in FIG. 7A, that is, directly over gas jet 140, which creates the Venturi effect, with nebulization occurring.

The aerosol from the nebulization then travels downward slightly after nebulization in the Venturi section (FIG. 2) (arrows 304). The slight downward dip is needed to clear the lower rim 111 of internal body 110. The aerosol then travels upward (arrows 305) in upper output airway 102 and around the exterior of internal body 110 (arrows 306) to exit port 182, through exit stem 184 and into the mouthpiece 190 (arrows 308). The gas channel defined by exit port 182, stem 184, and the interior of mouthpiece 190 is the output airway 180. The aerosol travels through airway 180 and is inhaled by the patient (arrow 310), which delivers the drug in the drug solution 124 to the lungs of the patient.

Control of the aerosol droplet size is important and is controlled by the nature of the nebulization in the Venturi section and the path taken by the aerosol after nebulization and prior to inhalation. Ideal droplets are in the range of about 0.5 μm to 5.0 μm (microns) in diameter, with an optimal size of around 2.0 μm.[1] Larger droplet sizes, if ingested into the mouth, have a tendency to stick to surfaces in the mouth and throat and are not ingested into the small airways of the lungs. Smaller droplet sizes remain in suspension in the inhaled air flow and effectively reach the small airways and alveoli of the lungs.

[1] Joachim Heyder, "Deposition of inhaled particles in the human respiratory tract and consequences for regional targeting in respiratory drug delivery," Proc Am Thorac Soc. 2004; 1(4):315-20. doi: 10.1513/pats.200409-046TA; Yung Sung Cheng, "Mechanisms of Pharmaceutical Aerosol Deposition in the Respiratory Tract," AAPS PharmSciTech. 2014 June; 15(3): 630-640, doi: 10.1208/s12249-014-0092-0. These references seem to suggest that for deposition of particles in the alveoli and small airways, there is also a maxima at about 0.02 μm, but in practice, this particle size is too small and will be exhaled efficiently before arriving at the small airways.

In the inventive design, larger aerosol droplets produced in the Venturi section are trapped by a combination of features, including the downward dip 304 in the aerosol path, and the need for the aerosol to rise up the level of output port 182. In addition, secondary baffles 186 and 188 may be provided as part of the internal body, that provide obstacles in the output airway 102 to help ensure that only appropriately sized droplets make their way to output airway 180. Further, by the nature of the design, any larger droplets or liquid exiting the liquid jet orifice 154 will tend to fall down into reservoir 122, thereby conserving the liquid medicament solution.

On exhalation (FIG. 3) air pressure rises in the interior of the nebulizer, which closes one-way inhalation valve 116. Exhalation gases (arrow 320) are vented through one-way exhalation valve 182 (arrows 322). Also illustrated are arrows 324 and 326 showing internal gases that may be aspirated toward the exhalation valve.

In an embodiment, the inventive nebulizer may be equipped with a continuous nebulization mode. As illustrated in the figures, the two nebulization modes (breath actuated and continuous) are controlled by selector knob 172, which has two positions in this embodiment. In the embodiment shown in FIG. 4B, selector knob 180 allows the diaphragm to flex as described in the preceding paragraphs for breath-actuated nebulization. In the embodiment shown in FIG. 4C, the selector knob 180 is shown rotated about 60° clockwise. In this position, a latch 186 (or equivalent mechanical linkage) pushes the diaphragm inward toward the Venturi and locks it into position, which pushes baffle member 162 in the position as shown in FIG. 7A, so that nebulization is continuous. As shown in the figures, the selector is mounted on collar 174 that juts off upper body 100 and houses the diaphragm 172.

The top of the nebulizer comprises cap 114 that fits over internal body 110 and upper body 110. Cap 114 includes a inhalation port 116 for ingestion of ambient air, and a one-way inhalation valve 118. As illustrated, valve 118 is a flap that opens downward during inhalation to allow air to enter the nebulizer. When inhalation stops, the flap returns a default or resting position that blocks air inside the nebulizer from exiting through port 116.

Figure 12:
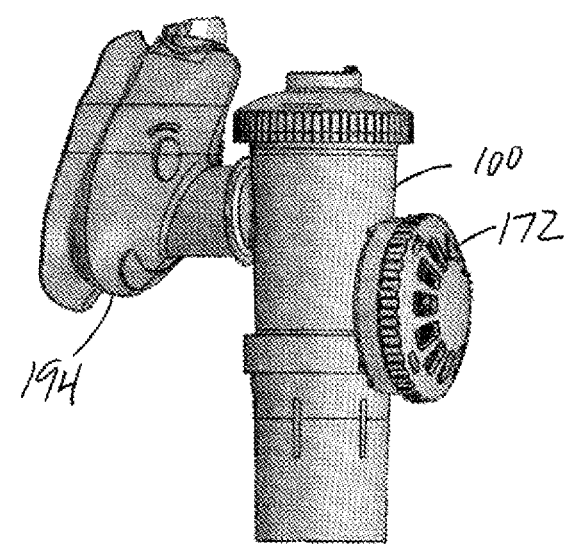
FIG. 12 is a perspective view of an embodiment of the inventive nebulizer with an inhalation mask.

In the embodiment illustrated in FIGS. 1-5 employs a simple mouthpiece attachment 190 that a patient would insert into their mouth. When the patient inhales, the aerosol is ingested into the patient through mouthpiece 190. Other embodiments include the use of a mask 194 as shown in FIG. 12. This is useful for patients who are too young, unconscious, or incompetent to keep a mouthpiece in their mouth and wrap their lips around the mouthpiece.

Figure 9:
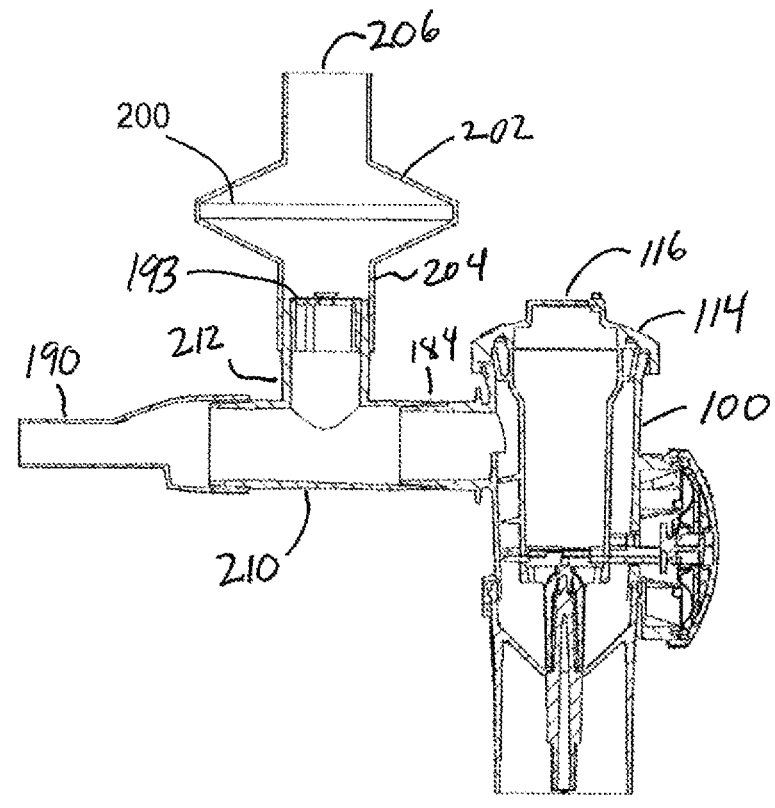
FIG. 9 is a cross section of an embodiment of the inventive nebulizer with an exhalation filter at a right angle to the airway.
Figure 10:
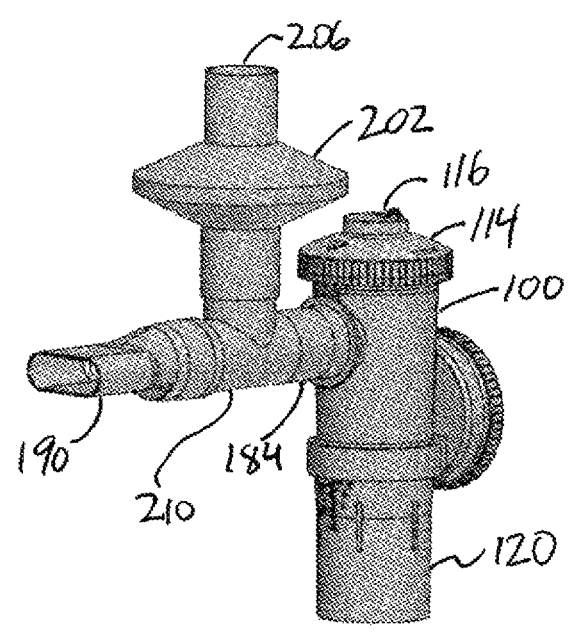
FIG. 10 is a perspective view of an embodiment of the inventive nebulizer with an exhalation filter at a right angle to the airway.
Figure 11:
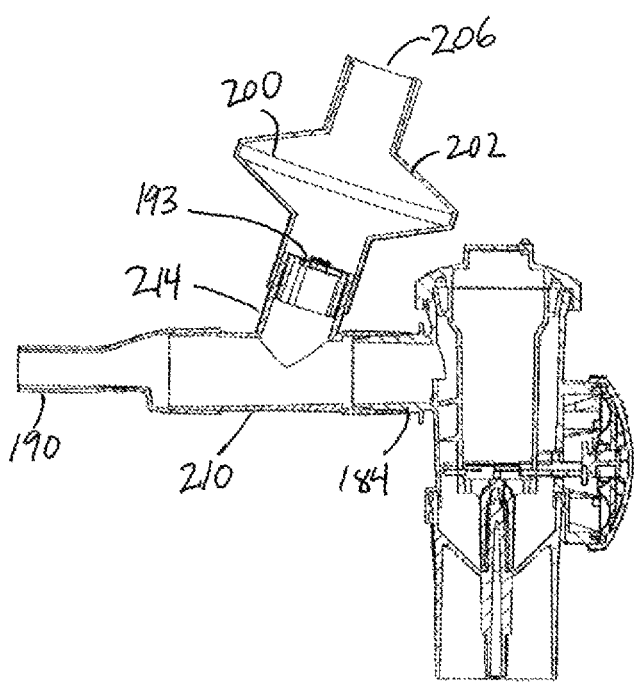
FIG. 11 is a cross section of an embodiment of the inventive nebulizer with an exhalation filter at an angle relative to the airway.

Another embodiment of the inventive nebulizer employs an exhalation filter 200 situated in housing 202. As shown in FIGS. 9-11, the exhalation filter may be mounted on a T-fitting 210 interposed between exit stem 184 and mouthpiece 190. The filter housing includes entry port 204 and exit port 206 open to ambient air. As illustrated in FIGS. 9-11, exhalation filter entry port 204 fits over branch 212 of the T-fitting. Embedded within branch 212 is a one-way exhalation filter 193, that only allows exhalation air to pass through to exhalation filter 200. During inhalation, outside air from port 206 cannot pass the exhalation filter 193, and the inhaled air and aerosol mixture cannot pass through either. Note that exhalation filter 192 is not used in the embodiment of FIGS. 9-11.

The purpose of exhalation filter 200 is to trap infection particles and aerosols in the exhalate from the patient. It is well known not that infectious disease particles, particularly from COVID-19, are present in exhaled air and are a significant vector for disease transmission.[2] Other diseases also can be transmitted from droplets in exhaled air, for example influenza.[3] Thus, the use of an exhalation filter that can trap exhaled infectious viral particles and aerosols can significantly improve the safety of the inventive nebulizer to surrounding persons and care givers, including doctors, nurses, and respiratory therapists.

[2] "COVID-19 Overview and Infection Prevention and Control Priorities in non-US Healthcare Settings" https://www.cdc.gov/coronavirus/2019-ncov/hcp/non-us-settings/overview/index.html, updated Aug. 12, 2020.
[3] Ben Killingley and Jonathan Nguyen-Van-Tam 'Routes of influenza transmission, "Influenza Other Respir Viruses. 2013 September; 7(Suppl 2): 42-51, doi: 10.1111/irv.12080.

In an embodiment, the exhalation filter 200 is a filter such as the ViroMax™ bacterial-viral filter or a similar device available from Ventlab-SunMed and others. Such a filter is designed to trap aerosolized infectious agents, such as bacteria and viruses in exhaled air from a patient. In addition, this filter can trap aerosol water droplets that carry infectious agents. These filters have a tubular connector on either side of the filter housing.

In an embodiment, the branch 212 of T-connector 210 leading to filter 200 is at a right angle, as shown FIGS. 9 and 10. In an embodiment (FIG. 11) the branch T-connector 210 leading to filter 200 is angled away at about a 70° angle with respect to the nebulizer, thereby angling the filter away from the face of the patient. This is shown as branch 214.

Exhalation filters have been disclosed in the past on nebulizers, for example to trap exhaled drugs that may cause harm to surrounding persons. See e.g., WO WO2015/009920 and J. Samuel and G. Smaldone, "Maximizing Deep Lung Deposition in Healthy and Fibrotic Subjects During Jet Nebulization," J. Aerosol Med. Pulmonary Drug Delivery, 2020, 33, 1-8, DOI: 10.1089/jamp.2019.1552.

| List of parts | |
|---|---|
| 100 | upper body |
| 102 | output upper chamber airway |
| 110 | internal body - upper |
| 111 | Lower rim of upper internal body |
| 112 | input upper chamber airway |
| 114 | cap |
| 116 | Inhalation input port |
| 118 | one-way inhalation valve |
| 120 | Lower body |
| 122 | liquid reservoir |

-continued

| List of parts | |
|---|---|
| 124 | medicament solution |
| 130 | Pressurized air inlet port |
| 132 | Pressurized air inlet tube |
| 133 | Top of pressurized air inlet tube |
| 134 | Pressurized air channel |
| 136 | Pressurized air flow |
| 140 | gas jet |
| 142 | Venturi section |
| 144 | Venturi surface |
| 150 | liquid channel |
| 152 | Liquid inlet port |
| 154 | Liquid jet orifice |
| 156 | Stem on internal body defining liquid channel |
| 160 | horizontally movable baffle |
| 161 | Other part of baffle head that does not cause the Venturi effect |
| 162 | Baffle member |
| 164 | Mechanical linkage of baffle member and diaphragm |
| 166 | Baffle rail |
| 168 | Baffle head section |
| 170 | Diaphragm |
| 172 | Selector knob |
| 174 | Selector knob collar |
| 180 | Output airway |
| 182 | Exit port for aerosol in upper body. |
| 184 | Exit stem |
| 186 | Secondary baffles on internal body |
| 188 | Secondary baffles on internal body |
| 190 | Mouthpiece |
| 192 | One-way exhalation filter |
| 193 | Exhalation filter with exhalation filter embodiment |
| 194 | Inhalation mask |
| 200 | Exhalation filter |
| 202 | Exhalation filter housing |
| 204 | Exhalation filter entry port |
| 206 | Exhalation filter exit port |
| 210 | T connector |
| 212 | Branch of the T-connector connecting to exhalation filter |
| 214 | Branch (angled) of the T-connector connecting to exhalation filter |
| 300 | Air entering nebulizer |
| 302 | Air flow in input airway 112 |
| 304 | Aerosol path after nebulization - downward dip under lower rim 111 |
| 305 | Aerosol path upward in airway 102 |
| 306 | Aerosol path horizontally around internal body 110 |
| 308 | Aerosol path in output airway 180 |
| 310 | Aerosol path into the mouth of the patient |
| 320 | Exhalation path |
| 322 | Exhalation air exiting from exhalation valve |
| 324 | Gases in the interior of the nebulizer being aspirated towards the exhalation valve. |
| 326 | Gases in the interior of the nebulizer being aspirated towards the exhalation valve. |

The invention claimed is:

1. A breath actuated nebulizer for the administration of inhaled medication to a patient only during the inhalation portion of a breathing cycle, comprising a. an upper body positionable in a vertical orientation, said upper body defining an output upper chamber airway, with an internal body nested within the upper body, wherein the internal body defines an input upper chamber airway, and having a one-way inhalation valve at the top of the input upper chamber airway;

b. a lower body positionable in a vertical orientation, said lower body having a chamber therein defining a liquid reservoir in which a medicament solution may be contained, wherein said liquid reservoir defines a horizontal axis;

c. a pressurized air inlet port in fluid communication with a gas jet at the interface of the upper body and the lower body wherein the gas jet is aimed in a center of the input upper airway;

d. a liquid channel adjacent to the gas inlet port, wherein the bottom of the liquid channel is in fluid communication with the liquid reservoir and the top of the liquid channel is a liquid orifice adjacent to the gas jet;

e. a baffle moveable between a first position and a second position, said baffle, when in the first position, being a predetermined distance from the gas jet such that a pressure differential is created in the liquid channel that draws the medicament solution through the liquid channel and causes nebulization of the medicament solution by the interaction of the gas jet and liquid orifice;

f. wherein the baffle, when in the second position, being distal from the gas jet so that the pressure differential in the liquid channel is insufficient to draw the medicament solution into the liquid channel, and no nebulization of the medicament solution occurs;

g. wherein the baffle moves in a channel between the first and second positions at a fixed distance relative to the gas jet;

h. wherein the baffle is moved from the second position to the first position in response to the motion of a diaphragm that moves in response to the inhalation by the patient, wherein the diaphragm is in mechanical communication with the baffle and the diaphragm movement during inhalation moves the baffle to the first position, and i. the diaphragm defaults to the second position when the patient is not inhaling;

j. whereby, the breath actuated nebulizer is operable to cause a medicament solution that has been dispensed into the liquid reservoir to become nebulized and delivered through the output airway of the nebulizer device in response to the application of negative pressure upon the output airway; and k. wherein the nebulizer further comprises a two-position selector mechanism that locks the diaphragm, with a first selector position in which the diaphragm moves in response to the breathing of the patient, and a second selector position in which the diaphragm is locked, and wherein in the second selector position the baffle is in the first baffle position.

2. The nebulizer of claim 1 wherein a mouthpiece is connected to the output airway and a one-way exhalation is valve is on the output airway, such that the nebulized medicament solution is transmitted through the mouthpiece during inhalation.

3. The nebulizer of claim 1 wherein a mouthpiece is connected to the nebulizer output airway and wherein an exhalation filter is in fluid communication with the output airway via a T-connector, and wherein a one-way exhalation filter is interposed between the airway and the exhalation filter.

4. The nebulizer of claim 3, wherein the exhalation filter is at a right angle to the output airway, or where the exhalation filter is angled at approximately 70° away from the face of the patient.

5. The nebulizer of claim 1 wherein an inhalation mask is connected to the nebulizer and the nebulized medicament solution is transmitted through the inhalation mask during inhalation.

6. The nebulizer of claim 1 wherein an audio signal is produced when the baffle moves from the first position to the second position.

7. The nebulizer of claim 6 wherein the audio signal is a clicking sound produced by a trigger contacting a part of the side cover.

8. The nebulizer of claim 1 wherein, during operation of the nebulizer, said gas jet and liquid orifice are on a same horizontal plane.

9. The nebulizer of claim 1 wherein the liquid orifice comprises one or more holes on top of the liquid channel.

10. The nebulizer of claim 1 wherein the liquid orifice comprises a concentric tubular opening in a concentric relationship to the gas jet.

11. The nebulizer of claim 1 wherein the baffle is responsive to inspiratory flow velocity in the range of 0.5 L/min to 15 L/min.

12. The nebulizer of claim 1 wherein the one-way inhalation valve permits ambient air to enter the nebulizer during inhalation.

13. The nebulizer of claim 1 further comprising an inhalation mask or mouthpiece in fluid communication with the airway, wherein an exhalation valve is present on the airway.

14. A method of administering an inhaled medicament to a patient by use of the nebulizer device of claim 1, said method comprising:

dispensing a medicament solution into the liquid reservoir; and causing the patient to inhale through the output airway, thereby applying said negative pressure to the output airway and causing nebulized medicament solution to be delivered through the output airway and to the patient.

15. The method of claim 14 wherein a mouthpiece is connected to the output airway and the patient inhales through the mouthpiece.

16. The method of claim 14 wherein a mask is connected to the output airway and the patient inhales through the mask.

* * * * *